United States Patent
Sharma et al.

(10) Patent No.: US 12,018,247 B2
(45) Date of Patent: Jun. 25, 2024

(54) METHODS AND KITS FOR NUCLEIC ACID PURIFICATION AND OTHER PROCEDURES

(71) Applicant: LuminUltra Technologies Ltd., Fredericton (CA)

(72) Inventors: Neil Sharma, Gaithersburg, MD (US); Wei Huang, Ellicott City, MD (US)

(73) Assignee: LuminUltra Technologies Ltd., Fredericton (CA)

( * ) Notice: Subject to any disclaimer, the term of this patent is extended or adjusted under 35 U.S.C. 154(b) by 850 days.

(21) Appl. No.: 17/068,453

(22) Filed: Oct. 12, 2020

(65) Prior Publication Data
US 2021/0180042 A1 Jun. 17, 2021

Related U.S. Application Data

(63) Continuation of application No. PCT/CA2019/050440, filed on Apr. 11, 2019.

(60) Provisional application No. 62/655,864, filed on Apr. 11, 2018.

(51) Int. Cl.
*C12N 15/10* (2006.01)

(52) U.S. Cl.
CPC .............................. *C12N 15/1006* (2013.01)

(58) Field of Classification Search
None
See application file for complete search history.

(56) References Cited

FOREIGN PATENT DOCUMENTS

| WO | WO-2007008093 A2 * | 1/2007 | ............. A61K 39/12 |
| WO | 2017044827 A1 | 3/2017 | |

OTHER PUBLICATIONS

Fauley, Arch Intern Med (Chic). 1941; 67(3):563-578. (Year: 1941).*
Dessev, Analytical Biochemistry 53, 269-271 (1973). (Year: 1973).*
International Search Report and Written Opinion of the International Searching Authority dated Jun. 19, 2019, for International Application No. PCT/CA2019/050440.
Mustafa, 1. et al., "Removal of Humic Acid from Peat Soils by using AlC13 prior to DNA 1-43 extraction". AIP Conference Proceedings, May 17, 2017 (May 17, 2017), vol. 1844(030007), ISSN: 1551-7616, <https://doi.org/10.1063/1.4983434>.

* cited by examiner

*Primary Examiner* — Layla D Berry
(74) *Attorney, Agent, or Firm* — Mayback IP Law, P.A.; Gregory L. Mayback

(57) ABSTRACT

A method of binding a nucleic acid and/or a contaminant from a sample includes the step of contacting the nucleic acid and/or the contaminant with a metal-based gel. The metal-based gel is preferably an aluminum-based gel, a cesium-based gel, a lanthanum-based gel, or a combination thereof. The phosphate concentration, phosphate:metal ratio, and/or pH in the sample is modulated during binding to influence the binding capacity and/or preference of the gel.

19 Claims, 7 Drawing Sheets
(7 of 7 Drawing Sheet(s) Filed in Color)

METHODS AND KITS FOR NUCLEIC ACID PURIFICATION AND OTHER PROCEDURES

CROSS-REFERENCE TO RELATED APPLICATIONS

This is a continuing application, under 35 U.S.C. § 120, of copending international application No. PCT/CA2019/050440, filed Apr. 11, 2019, which designated the United States and was published in English; this application also claims the priority, under 35 U.S.C. § 119, of U.S. Provisional Patent Application Ser. No. 62/655,864, filed Apr. 11, 2018; the prior applications are herewith incorporated by reference in their entirety.

STATEMENT REGARDING FEDERALLY SPONSORED RESEARCH OR DEVELOPMENT

Not Applicable

FIELD OF THE INVENTION

The present systems, apparatuses, and methods lie in the field of nucleic acid purification, and more particularly to methods and uses of metal gels, and kits including said gels, for nucleic acid purification.

BACKGROUND OF THE INVENTION

Extracting and purifying nucleic acids including DNA and RNA from samples, for example, from tissue, blood, urine, stool, soil, environmental, and other materials is often desirable. Purifying the nucleic acid facilitates any subsequent procedures, such as polymerase chain reaction (PCR) and nucleic acid sequencing. The success and accuracy of those analyses may be highly dependent on the nucleic acids being relatively purified, that is, free of enzymatic and/or chemical inhibitors, such as humic acids and other natural and man-made contaminants.

Many approaches have been used to purify nucleic acids from different materials in both the literature and commercially with various degrees of success. These approaches include methods to selectively solubilize, precipitate, and adsorb contaminants and/or nucleic acids.

Despite the development of a multitude of approaches to nucleic acid purification over the past several decades, however, there is still a need for better and more robust methods, especially for complex and highly contaminated samples. Some of the prior art methods, for example, may be overly invasive and destructive of the sample. For example, some techniques remove significant amounts of nucleic acids along with the contaminants during the purification process, which potentially decreases the sample to the point where subsequent use is limited or impossible. As another example, other contaminants may interfere with a purifying process, such as when soluble metal salts are used in a flocculation process to precipitate and remove impurities. This process may be problematic because it may be inhibited in the presence of common chelating agents (e.g., ethylenediaminetetraacetic acid (EDTA)).

SUMMARY OF THE INVENTION

The systems, apparatuses, and methods described provide a method of binding a nucleic acid and/or a contaminant from a sample comprising the step of contacting the nucleic acid and/or the contaminant with a metal-based gel, a kit for binding a nucleic acid and/or a contaminant from a sample comprising a metal-based gel, and a kit for binding a nucleic acid and/or a contaminant from a sample comprising reagents to prepare a metal-based gel that overcome the hereinafore-mentioned disadvantages of the heretofore-known devices and methods of this general type.

According to yet another aspect, there is provided a method for binding contaminants from a nucleic acid containing sample by using a metal-based gel while minimizing simultaneous binding of nucleic acid to the gel comprising the steps of introducing the gel to the sample; modulating the phosphate concentration, phosphate:metal ratio, and/or solution pH in the sample to selectively release the nucleic acid.

According to a further aspect, there is provided a use of a metal-based gel for binding nucleic acid and/or a contaminant from a sample.

The metal-based gel may be an aluminum-based gel, a cesium-based gel, a lanthanum-based gel, or a combination thereof. More specifically, the metal-based gel may be an aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

Preferably, the phosphate concentration, ratio of phosphate:metal in the gel, and/or pH in the sample is modulated during the binding. The concentration of phosphate in the sample during the contacting may be adjusted between 2 mM to 200 mM. The pH of the sample during the binding may be 2 to 11. The molar ratio of phosphate to metal in the gel during the binding may be 10:1 to 1:100.

With the foregoing and other objects in view, there is provided, a method of binding a nucleic acid and/or a contaminant from a sample comprising the step of contacting the nucleic acid and/or the contaminant with a metal-based gel.

In accordance with another mode, the metal-based gel is an aluminum-based gel, a cesium-based gel, a lanthanum-based gel, or a combination thereof.

In accordance with a further mode, the metal-based gel is an aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

In accordance with an added mode, there is provided the step of modulating the phosphate concentration, the phosphate:metal ratio, and/or the pH in the sample during the contacting.

In accordance with an additional mode, the concentration of phosphate in the sample during the contacting is 2 mM to 200 mM.

In accordance with yet another mode, the pH of the sample during the contacting is 2 to 11.

In accordance with yet a further mode, a molar ratio of phosphate to metal in the gel during the contacting is 10:1 to 1:100.

In accordance with yet an added mode, there is provided the step of separating the metal-based gel from the sample.

In accordance with yet an additional mode, there is provided the step of recovering the nucleic acid in a supernatant.

In accordance with again another mode, there is provided the step of eluting the nucleic acid from the gel in a solution.

In accordance with again a further mode, the metal-based gel is prepared before the contacting step.

In accordance with again an added mode, reagents to prepare the metal-based gel are added to the sample to form the metal-based gel during the contacting step.

In accordance with again an additional mode, the reagents comprise a metal salt, a base, a phosphate, or a combination of base and phosphate.

In accordance with still another mode, the metal salt comprises aluminum chloride, aluminum ammonium sulfate, aluminum potassium sulfate, aluminum chlorohydrate, aluminum sulfate, other aluminum salts, lanthanum chloride, lanthanum sulfate, lanthanum bromide, other lanthanum salts, cesium chloride, cesium sulfate, cesium bromide, other cesium salt, or any combination thereof.

In accordance with still a further mode, the metal-based gel comprises gels composed of metals that have a $3^+$ charge.

With the objects in view, there is also provided a method for binding contaminants from a nucleic acid containing sample by using a metal-based gel while minimizing simultaneous binding of nucleic acid to the gel comprising the steps of introducing the gel to the sample and modulating the phosphate concentration, phosphate:metal ratio, and/or solution pH in the sample to selectively bind the contaminants.

In accordance with still an added mode, the metal-based gel is aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

With the objects in view, there is also provided a use of a metal-based gel for binding nucleic acid and/or a contaminant from a sample.

In accordance with still an additional mode, the metal-based gel is an aluminum-based gel, a cesium-based gel, a lanthanum-based gel, or a combination thereof.

In accordance with another mode, the metal-based gel is aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

In accordance with a further mode, the phosphate concentration, phosphate:metal ratio, and/or pH in the sample is modulated during binding.

In accordance with an added mode, the concentration of phosphate in the sample during binding is 2 mM to 200 mM.

In accordance with an additional mode, the pH of the sample during binding is 2 to 11.

In accordance with yet another mode, a molar ratio of phosphate to metal in the gel is 10:1 to 1:100.

With the objects in view, there is also provided a kit for binding a nucleic acid and/or a contaminant from a sample comprising a metal-based gel.

In accordance with yet a further feature, the metal-based gel is an aluminum-based gel, a cesium-based gel, a lanthanum-based gel, or a combination thereof.

In accordance with yet an added feature, the metal-based gel is an aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

In accordance with yet an additional feature, there is provided a phosphate-containing solution to modulate the concentration of phosphate from 2 mM to 200 mM in the sample during the binding.

In accordance with again another feature, there is provided a phosphate-containing solution to modulate a molar ratio of phosphate to metal in the gel from 10:1 to 1:100 during the binding.

In accordance with again a further feature, there is provided a pH buffer, an acid, and/or a base for modulating the pH from 2 to 11 in the sample during the binding.

In accordance with again an added feature, the gel is stabilized in the kit using an excipient and/or freeze-drying.

In accordance with again an additional feature, there is provided a lysis solution, a binding buffer, a wash solution, an eluting solution, spin columns, additional binding resin, or any combination thereof.

In accordance with still another feature, there is provided instructions outlining how to integrate the metal-based gel into known nucleic acid purification protocols and/or kits.

With the objects in view, there is also provided a kit for binding a nucleic acid and/or a contaminant from a sample comprising reagents to prepare a metal-based gel.

In accordance with still a further feature, the reagents comprise a metal salt, a base, a phosphate, or a combination of base and phosphate to be reacted to form the metal-based gel.

In accordance with still an added feature, the metal salt comprises aluminum chloride, aluminum ammonium sulfate, aluminum potassium sulfate, aluminum chlorohydrate, aluminum sulfate, other aluminum salts, lanthanum chloride, lanthanum sulfate, lanthanum bromide, other lanthanum salts, cesium chloride, cesium sulfate, cesium bromide, other cesium salt, or any combination thereof.

In accordance with still an additional feature, the metal-based gel is an aluminum hydroxide gel, an aluminum phosphate gel, an aluminum hydroxyphosphate gel, a lanthanum hydroxide gel, a lanthanum phosphate gel, a lanthanum hydroxyphosphate gel, a cesium hydroxide gel, a cesium phosphate gel, a cesium hydroxyphosphate gel, or any combination thereof.

In accordance with another feature, at least one of the metal salt, the base, and the phosphate is mixed with a buffer.

In accordance with a further feature, there is provided a phosphate-containing solution to modulate the concentration of phosphate from 2 mM to 200 mM in the sample during the binding.

In accordance with an added feature, there is provided a phosphate-containing solution to modulate a molar ratio of phosphate to metal in the gel from 10:1 to 1:100 during the binding.

In accordance with an additional feature, there is provided a pH buffer, an acid, and/or a base for modulating the pH from 2 to 11 in the sample during the binding.

In accordance with yet another feature, there is provided a lysis solution, a binding buffer, a wash solution, an eluting solution, spin columns, additional binding resin, or any combination thereof.

In accordance with a concomitant feature, there is provided instructions outlining how to integrate the metal-based gel into known nucleic acid binding protocols and/or kits.

Although the systems, apparatuses, and methods are illustrated and described herein as embodied in a method of binding a nucleic acid and/or a contaminant from a sample comprising the step of contacting the nucleic acid and/or the contaminant with a metal-based gel, a kit for binding a nucleic acid and/or a contaminant from a sample comprising a metal-based gel, and a kit for binding a nucleic acid and/or a contaminant from a sample comprising reagents to prepare a metal-based gel, it is, nevertheless, not intended to be limited to the details shown because various modifications and structural changes may be made therein without departing from the spirit of the invention and within the scope and range of equivalents of the claims. Additionally, well-known elements of exemplary embodiments will not be described in detail or will be omitted so as not to obscure the relevant details of the systems, apparatuses, and methods.

BRIEF DESCRIPTION OF THE DRAWINGS

The patent or application file contains at least one drawing executed in color. Copies of this patent or patent application publication with color drawing9s) will be provided by the Office upon request and payment of the necessary fee.

The accompanying figures, where like reference numerals refer to identical or functionally similar elements throughout the separate views, which are not true to scale, and which, together with the detailed description below, are incorporated in and form part of the specification, serve to illustrate further various embodiments and to explain various principles and advantages all in accordance with the systems, apparatuses, and methods. Advantages of embodiments of the systems, apparatuses, and methods will be apparent from the following detailed description of the exemplary embodiments thereof, which description should be considered in conjunction with the accompanying drawings in which.

DETAILED DESCRIPTION OF THE EMBODIMENTS

Figure 1:
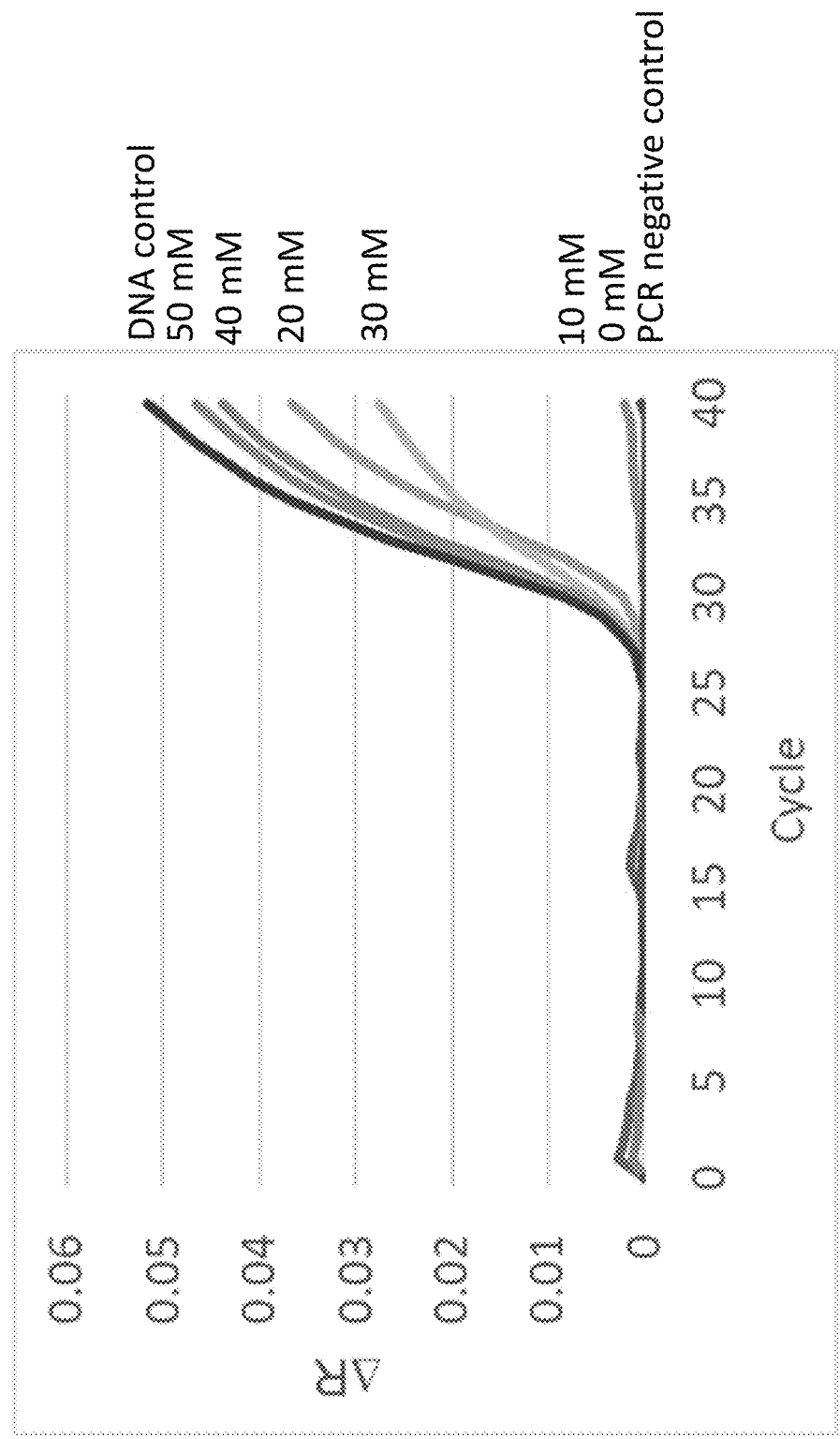
FIG. 1 is a plot illustrating the result various phosphate concentrations has on the binding specificity of a gel according to an exemplary embodiment.

A better understanding of the present methods, kits, and systems and their objects and advantages will become apparent to those skilled in this art from the following detailed description, wherein there is described only an exemplary embodiment, simply by way of illustration of the best mode contemplated for carrying out the invention. As will be realized, the present methods, kits, and systems are capable of modifications in various obvious respects, all without departing from the scope and spirit of the invention. Accordingly, the description should be regarded as illustrative in nature and not as restrictive.

As used herein, contaminant includes any chemical or physical substance that can potentially interfere with the purification of a nucleic acid from a sample, or that can potentially interfere with subsequent applications of the nucleic acid, purified or otherwise. A contaminant can be an organic or an inorganic molecule.

As used herein, the term nucleic acid includes any DNA, RNA or other nucleotide, or any analogue or derivative thereof. It may also include plasmids, cosmids, and other types of expression systems, and also viral DNA and RNA.

The methods, uses, and kits for nucleic acid purification and other procedures taught herein comprise the provision and use of metal-based gels to aid in the purification of nucleic acid. The type of metal-based gel and the binding conditions help to dictate whether the gels bind contaminants, nucleic acids, or both, which can then be subsequently removed from the sample solution.

In one exemplary embodiment, the metal-based gels include aluminum-based gels, lanthanum-based gels, cerium-based gels, or combinations thereof.

While the exemplary embodiments are primarily directed to aluminum, cerium, and lanthanum-based gels, other metal-based gels are also contemplated, including gallium-based gels, indium-based gels, iron-based gels, yttrium-based gels, scandium-based gels, as well as gels composed of other metals, and particularly those that have a $3^+$ charge. Hereinafter, the word "gels" or "gel" is used inclusively to refer to any and all types, except where a specific gel is referred to.

The gels are used in a nucleic acid purification process, apparatus, and/or are provided as part of a nucleic acid purification process or apparatus, including but not limited to new procedures, kits, and the like, and/or as a retrofit, supplement and the like to procedures or kits already known in the art or available in the marketplace.

A gel according to an exemplary embodiment is prepared by reacting a metal salt (e.g. aluminum chloride or lanthanum chloride) with, e.g., a base, a phosphate, or a combination of base and phosphate to form a metal hydroxide gel, a metal phosphate gel, or a metal hydroxyphosphate gel, which then is provided in solution during the purification process. Typically, the gels when prepared are generally insoluble under normal reaction conditions.

According to an exemplary embodiment, some of the gels taught herein may be prepared generally as follows, which creates a substantially insoluble gel under typical reaction conditions:

1) For aluminum-based gels:
   reacting an aluminum salt such as aluminum chloride, aluminum ammonium sulfate, aluminum potassium sulfate, aluminum chlorohydrate, aluminum sulfate, or other aluminum salt or mixture of salts;
   with a base, phosphate or combination of both;
   to produce an aluminum hydroxide gel, an aluminum phosphate gel, or an aluminum hydroxyphosphate gel, respectively;

2) For lanthanum-based gels:
   by reacting a lanthanum salt such as lanthanum chloride, lanthanum sulfate, lanthanum bromide, or other lanthanum salt or mixture of salts;
   with a base, phosphate or combination of both;
   to produce a lanthanum hydroxide gel, a lanthanum phosphate gel, or a lanthanum hydroxyphosphate gel, respectively;

3) For cesium-based gels:
   by reacting a cesium salt such as cesium chloride, cesium sulfate, cesium bromide, or other cesium salt or mixture of salts;
   with a base, phosphate or combination of both;

to produce a cesium hydroxide gel, a cesium phosphate gel, or a cesium hydroxyphosphate gel, respectively;

4) For aluminum-lanthanum combination gels:
by reacting an aluminum salt such as aluminum chloride, aluminum ammonium sulfate, aluminum potassium sulfate, aluminum chlorohydrate, aluminum sulfate, or other aluminum salt or mixture of salts;
with a lanthanum salt such as lanthanum chloride, lanthanum sulfate, lanthanum bromide, or other lanthanum salt or mixture of salts;
with a base, phosphate or combination of both;
to produce an aluminum-lanthanum hydroxide gel, an aluminum-lanthanum phosphate gel, or an aluminum-lanthanum hydroxyphosphate gel, respectively.

Different combination gels, such as aluminum-cesium and lanthanum-cesium can be produced in a similar manner to 4) above. In these embodiments, the relevant salts, i.e., aluminum and cesium, or lanthanum and cesium, are reacted with a base, phosphate, or combination of both.

It may be desired in certain embodiments to provide at least one additional component for incorporation with the gel structure. This can occur either during the preparation of the gels, or after the gels have been prepared. For example, sulfate can be used to substitute for some hydroxyls to form aluminum hydroxysulfate or aluminum hydroxyphosphate sulfate, or similar lanthanum- or cesium-based sulfates. Bases may be provided, including sodium hydroxide and sodium carbonate. Suitable phosphates may be provided as well, including monobasic, dibasic, and tribasic sodium phosphate.

Doping the gel, either during formation or afterward, using varying concentrations of phosphate ions and/or by controlling the solution pH may be desired according to some embodiments. These and other additives, reactants (for example polymers), and mixing conditions may produce gels with varying surface charges which may impact the adsorption properties of the gel. The resulting gel suspension can optionally be neutralized and/or the gel can be collected and washed to remove unreacted components, for buffer exchange before use, etc.

Modifying different parameters can provide gels with adjusted binding properties, that may be desirable for certain conditions. The adsorption properties of the gel can be modified in several ways:

By controlling the amount of base versus phosphate, either during preparation of the gel or after the gel has been prepared. Without being bound to theory, the amount of base versus phosphate incorporated into the gel may change the surface charge of the gel and/or affect its propensity toward ligand exchange thus changing the binding properties of the gel towards different target molecules.

By including other additives during the preparation or use of the gel such as sulfates, acetates, and synthetic or natural polymers such as polyacrylamide and polydiallyldimethylammonimn chloride. Without being bound to theory, these additives may incorporate into the gel through ligand exchange or modify the surface of the gel thus changing the binding properties of the gel towards different target molecules.

By adjusting the gel solution pH. Without being bound to theory, the pH may affect the surface charge on the gel and/or the charge on the target molecules and thus can change the binding properties of the gel towards different target molecules.

According to one exemplary embodiment, the gels may be prepared immediately or shortly prior to use. The components of the gel may be procured separately and mixed as discussed above. Alternatively, the components may come in the form of a kit, in which the end user withdraws and combines the necessary amounts of each component to form the gel.

In another exemplary embodiment, the gels are stabilized until use. In this exemplary embodiment, the gel may be stabilized by the user after the gel has been synthesized, or alternatively, a stabilized gel may come in the form of a kit. A suitable excipient is used to stabilize the gel, such as, for example, a solution containing a final concentration of about 20% trehalose. It is expected that those skilled in the art may use other excipients in place of trehalose such as mannitol, sucrose, polyvinylpyrrolidone, and other commonly used stabilizers. Supplemental phosphate and/or other components, such as those that modify or control pH, may also be added to the stabilized gel as desired to influence the downstream adsorption properties of the gel. The stabilized gel can be washed as needed to remove the excipient prior to use.

The gel may also be freeze-dried and then rehydrated prior to use. The gel may also be freeze dried with excipients.

An exemplary method of purifying a nucleic acid using a gel according to one exemplary embodiment comprises some or all of the following steps, in any order as desired. In this embodiment, the gel is added prior to separation of the cellular debris.

Cell lysis
Add buffer to control to desired pH
Add gel
Add phosphate to obtain desired concentration
Centrifuge to pellet: 1) cell debris and 2) gel with adsorbed contaminants
Transfer nucleic acid containing supernatant to a new tube
Add binding buffer
Bind nucleic acids to silica column
Wash silica column
Dry silica spin column
Elute nucleic acids from silica column into a new tube The following method according to another exemplary embodiment includes an initial separation of cellular debris prior to introducing the gel, which subsequently absorbs and precipitates contaminants. The method may include some or all of the following steps, in any order as desired.

Cell lysis
Centrifuge to pellet cell debris
Transfer nucleic acid containing supernatant to a new tube
Add gel
Add phosphate to obtain desired concentration
Centrifuge to pellet gel with adsorbed contaminants
Transfer nucleic acid containing supernatant to a new tube
Add binding buffer
Bind nucleic acids to silica column
Wash silica column
Dry silica column
Elute nucleic acids from silica column into a new tube It is appreciated that additional steps can be included in the above methods, such as washing steps using appropriate buffers as would be known in the art.

In the above examples and other embodiments, the cells are first lysed using chemical, physical, and/or enzymatic measures to release cell contents. Contaminants are captured during this step or in a subsequent step using a gel in solution. The composition of the gel, phosphate concentration and/or pH of the solution can be controlled to allow selective binding of contaminants without significant binding of nucleic acids. The gel—with bound contaminants—can subsequently be easily removed from the bulk solution containing the unbound nucleic acids by centrifugation or other measures (i.e., filtration). The nucleic acids may then be further purified by known methods, for example, by, e.g., binding to a silica column in the presence of a chaotropic agent, washed, and finally eluted into a new tube using a suitable elution reagent.

In another exemplary embodiment, the gel may be used to bind and release nucleic acid. Such an embodiment would be useful when, for example, nucleic acid has already been substantially purified, but a higher concentration of the nucleic acid is preferred for subsequent applications. At certain conditions the gel can be used in a nucleic acid purification method to bind nucleic acid, which can be ultimately be eluted from the gel in a smaller more concentrated volume.

Alternatively, a method according to another exemplary embodiment relies on the binding specificity of the gel. In this embodiment, the gel is incorporated into a nucleic acid purification method, and the conditions provide for nucleic acid along with other contaminants from a solution to be bound to the gel. The gel can be pelleted with the nucleic acid and contaminants still bound. By varying certain conditions in the eluent, such as pH and/or phosphate concentration, the nucleic acid can be relatively selectively released from the gel, while the contaminant remains bound.

According to one exemplary embodiment, a method for providing binding and release of nucleic acid may be as follows. The method may include some or all of the following steps, in any order as desired.

Add gel to solution containing dilute nucleic acid and optional contaminants
    Mix
    Centrifuge to pellet gel with bound nucleic acid
    Discard supernatant
    Wash gel with distilled water or buffer
    Resuspend gel in a small volume of buffer containing e.g. high concentration of phosphate to release bound nucleic acids
    Optionally: Add other agents such as sulfates, detergents, or chelators, and/or adjust pH or temperature to further assist with release of nucleic acids
    Centrifuge to pellet gel
    Collect supernatant containing nucleic acid According to another exemplary embodiment, the gel may also be used in procedures to at least partially remove cellular debris and other common insoluble components and/or contaminants in conjunction with other agents. For example, the gel may be used with other purifying agents, such as powdered activated charcoal (PAC). In particular, the gel can be added prior to centrifugation, settling, or other removal steps within purification procedures to aid in the efficient removal of other insoluble materials and/or contaminants. For example, a gel can be added before, simultaneously, or after treatment of a supernatant with another agent, such as PAC, to assist in the efficient removal of contaminants, as well as of the PAC.

According to one exemplary embodiment, an example of such a method is as follows, which may contain some or all of the steps, in any order as desired.

Cell lysis
    Centrifuge to pellet cell debris
    Transfer nucleic acid containing supernatant to a new tube
    Add buffer to control desired pH
    Add phosphate as desired
    Add PAC and Gel
    Centrifuge to pellet PAC and gel
    Transfer nucleic acid containing supernatant to a new tube
    Add binding buffer
    Bind nucleic acid to silica column
    Wash silica column
    Dry silica spin column
    Elute DNA from silica column into a new tube It is expected that somebody skilled in the art can develop or modify a multitude of different known protocols having different purification steps that can use the gel according to the present methods, kits, and systems, or otherwise incorporate the use of the gel into known nucleic acid purification protocols, including protocols associated with commercially available kits.

In another exemplary embodiment, the gel according to the present description is incorporated into a kit. The kit is preferably directed to isolating or purifying nucleic acid from an environmental or biological sample. The kit may comprise a gel according to an exemplary embodiment, or alternatively, the kit comprises the components required to make the gel. In another exemplary embodiment, at least one component required to make the gel, such as a metal salt, is incorporated into a solution or buffer provided in the kit, such as a lysis buffer. After the lysis buffer has been introduced to the sample, the remaining components necessary to prepare the gel can be added to the solution. Instructions describing a method for preparing the gel and/or integrating the gel into known nucleic acid isolation and purification methods can also be included. Such a kit would be useful in supplementing known isolation and purification methods and/or commercially available products.

Alternatively, the kit may be a standalone kit that in addition to including a gel according to an exemplary embodiment, comprises a plurality of additional components, including chemicals, solutions, tubes, columns, etc., which may be necessary for isolation and/or purification of nucleic acid from a sample. For example, the kit may include a lysis solution, a binding buffer, a wash solution, an eluting solution, spin columns, additional binding resin, or any combination thereof.

The experimental conditions influence the binding specificity of the gels. Adsorption through use of the gels may be applied to nucleic acids and other biological and non-biological molecules such as proteins and small compounds. For example, the amount of certain factors, such as phosphate, the pH, the temperature, necessary to confer the desired adsorption properties to the gel, i.e., binding nucleic acid, binding contaminants, or binding both, will vary depending on the specific gel, the application, and the experimental conditions.

In some cases, no phosphate may be used if it is desired that the gel fully adsorbs nucleic acids and/or other target molecules. In cases where it is desired that the gel adsorbs contaminants, but minimally adsorbs nucleic acids, a typical molar concentration of phosphate is expected to be in the range of 2 mM to 200 mM in many cases. However, under certain experimental conditions, higher or lower concentrations may be necessary to achieve the desired adsorption properties. In cases where it is desired that the gel adsorbs contaminants, but minimally adsorbs nucleic acids, a typical molar ratio of phosphate to metal (e.g., aluminum, cerium, or lanthanum) is expected to be in the range of 1:100 to 10:1. However, under certain experimental conditions, higher or lower ratios may be necessary to achieve the desired adsorption properties.

The pH range may influence what targets are bound to the gel. The pH affects the charge on the gel and/or the target molecules, thereby affecting the binding target of the gel. Preferably, the pH during binding can vary from 2 to 11 based upon the intended binding target of the gel.

Releasing nucleic acid bound to the gel, selectively or otherwise, can be performed by a number of measures. For example, providing a gel with little or no phosphate may result in nucleic acid adsorption onto the gel. The nucleic acid can be released by providing a suitable amount of phosphate or an equivalent and/or by optionally using other agents such as sulfates, detergents, or chelators and/or by adjusting pH or temperatures. For example, a molar ratio of phosphate to metal (e.g., aluminum, cerium, lanthanum) in the range of 10:1 to 1:100; a pH in the range of 2-11; temperature of 4° C. to 100° C.; detergent concentration of about 0.1% to 25% (w/v); and chelators in a concentration range of about 1 mM to 1000 mM, may be able to release nucleic acid from being bound by the gel.

Example 1

The phosphate concentration during binding impacts the desired adsorption properties of the gel. The phosphate concentration can be varied depending on the specific application and intended binding target.

Phosphate ions or equivalents in a suitable concentration can be provided and modified in the gel or in the gel binding environment in several ways, such as, e.g.:
- During the initial preparation of the gel by including a source of phosphate ions, potentially in excess as needed;
- Pre-treating a gel such as aluminum hydroxide or lanthanum hydroxide with a solution containing phosphate ions before use in nucleic acid purification procedures. The resulting gel can optionally be washed to remove unbound and excess components; and
- Providing phosphate ions in the nucleic acid containing solution prior to, simultaneously with, or after being mixed with the gel.

The effect of various phosphate concentrations on the binding specificity and capacity of the gel was investigated. Briefly, solutions containing identical amounts of humic acid and DNA were treated with an identical volume of aluminum hydroxide gel and varying concentrations of phosphate ranging from 10 mM-50 mM. After a short mixing period, the gel was pelleted, and a portion of the supernatant was subjected to qPCR to analyze the amount of unbound DNA following treatment and binding with the aluminum hydroxide gel. FIG. 1 shows that the aluminum hydroxide binds the DNA in the absence of, or at very low concentrations (10 mM) of, phosphate. Effective removal of humic acid without significant removal of DNA was found in suitable phosphate concentrations starting at 20 mM-30 mM in this particular example.

Example 2

The effect of the molar ratio of phosphate to the $La^{3+}$ in the gel during adsorption was investigated.

Briefly, lanthanum phosphate gel was made by mixing 100 μl of phosphate solution (100 mM, pH 7.5) with 10 μl, 5 μl, 3.3 μl, or 2.5 μl of $LaCl_3$ solution (1M) in individual tubes. The resulting ratios of $PO_4^{3-}:La^{3+}$ were 1:1, 2:1, 3:1, and 4:1, respectively. Each tube received 10 μl Control DNA solution, 8 μl Humic Acid solution (12 mg/ml), up to 500 μl water, and vortexed to mix. After 10 minutes of mixing at room temperature, the tubes were spun down, and 1 μl of the supernatant from each tube was subject to qPCR.

Figure 2:
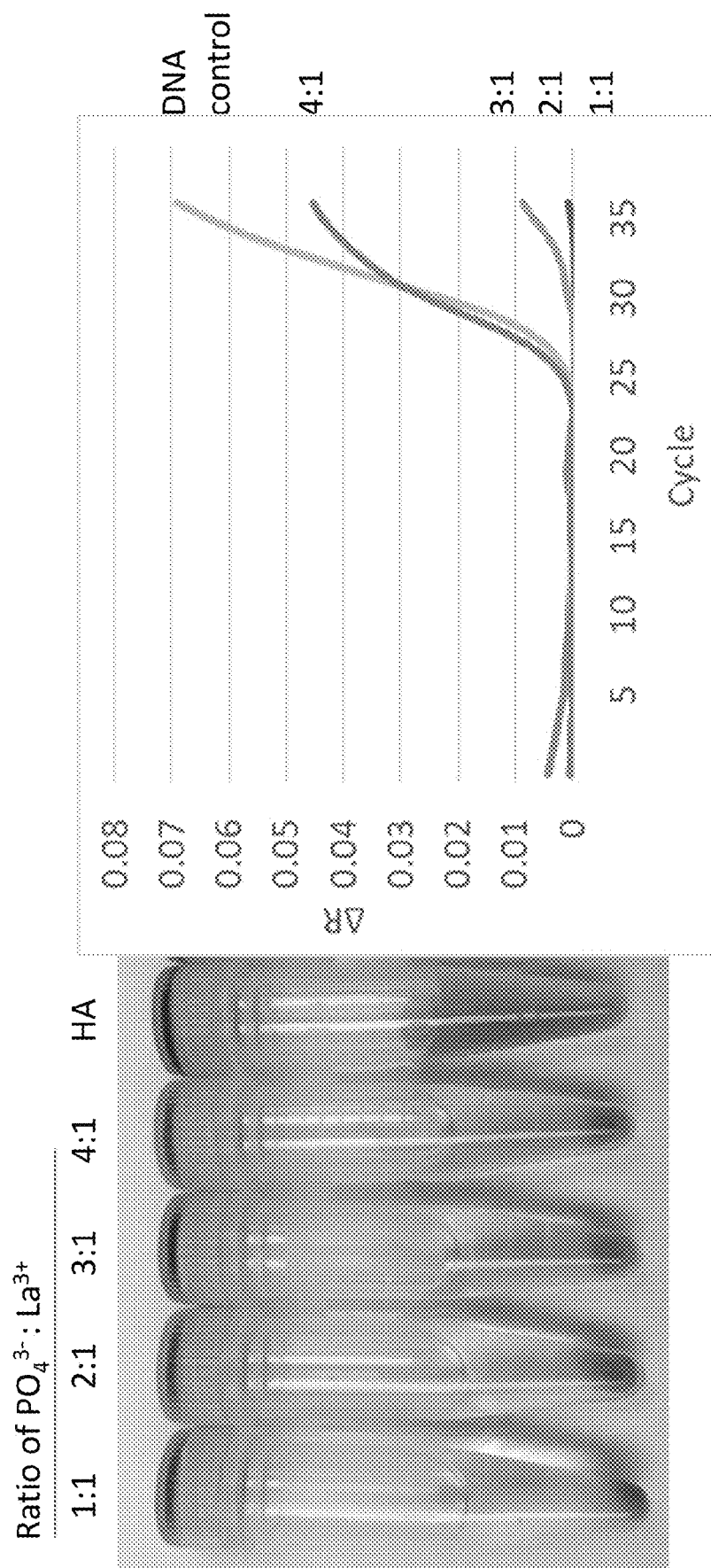
FIG. 2 is a photo and plot illustrating the result various phosphate to metal ratios have on the binding specificity of a gel according to an exemplary embodiment.

As can be seen from FIG. 2, a higher ratio of $PO_4^{3-}:La^{3+}$ results in effective removal of humic acid without significant removal of DNA.

Example 3

The pH of the binding solution may impact the binding specificity and capacity of the gels. This can be manipulated based on the intended binding target of the gel.

Solution pH can be modulated in several ways at various points during the purification process, including prior to, during, or after the sample solution is mixed with the gel including, e.g.:
- Using a suitable biological buffer such as Tris, HEPES, phosphate, or other buffers composed of other chemicals in specific ratios to achieve the desired pH of the binding solution;
- Adjusting the solution temperature when using buffers that are temperature sensitive;
- Using acids and/or bases such as HCl, NaOH or other chemicals to adjust solution to achieve the desired pH.

Figure 3:
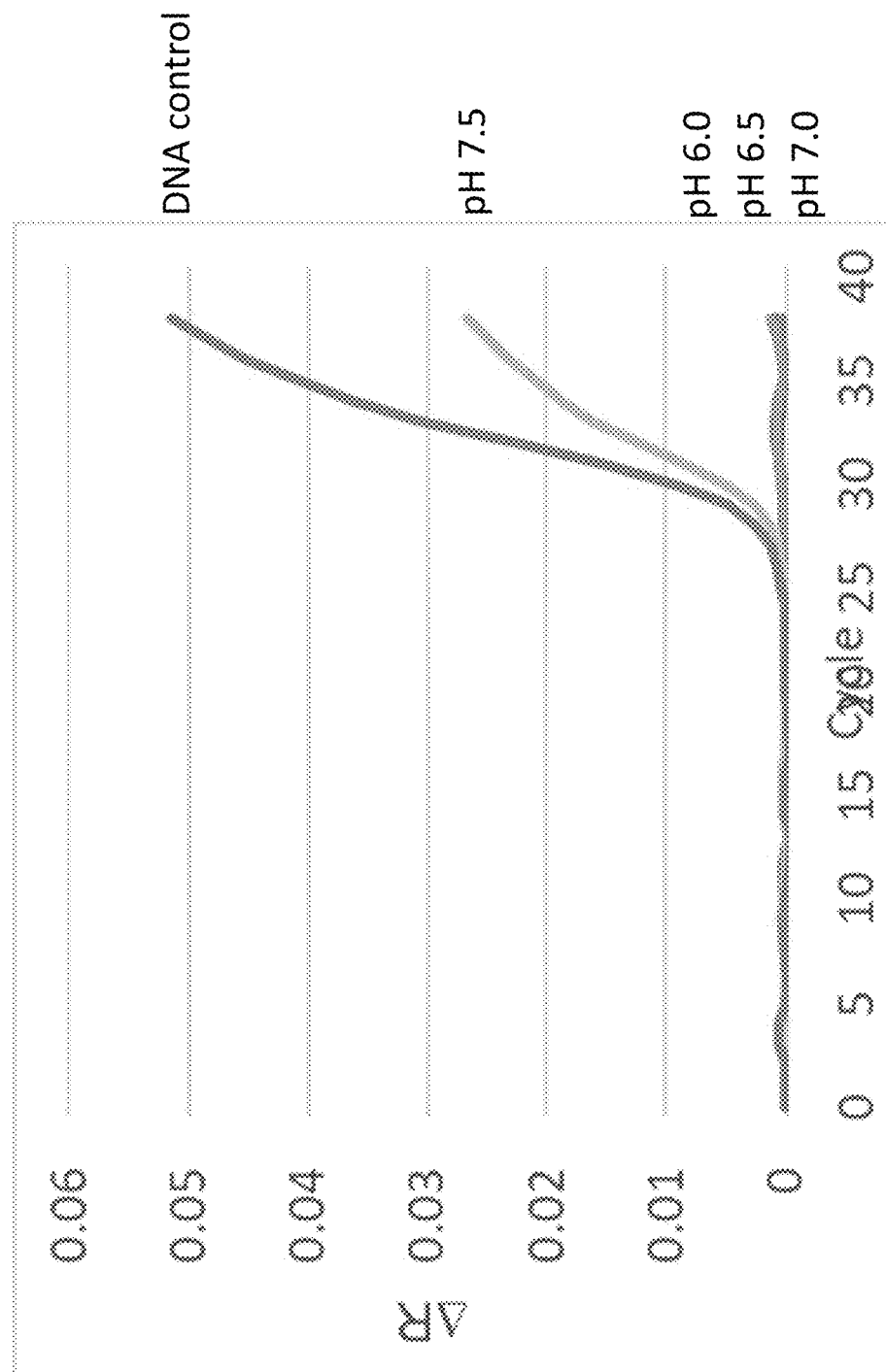
FIG. 3 is a plot illustrating the result various pH has on the binding specificity of a gel according to an exemplary embodiment.

In this example, the impact of a varied solution pH at a constant phosphate concentration was observed. Briefly, solutions containing identical amounts of humic acid and DNA were mixed with an identical volume of lanthanum-based gel with a solution pH varying between 6-7.5. After a short period, the gel was pelleted, and a fraction of the supernatant was subjected to qPCR to analyze the amount of unbound DNA. The results can be seen in FIG. 3, which shows that a pH of about 7.5 achieved good humic acid absorption by the gel without significant DNA binding, which occurred at lower pH values.

Example 4

Exemplary embodiments may make use of the effects of varying phosphate concentration and/or pH on modifying the adsorption properties of the gel as described herein to provide capture and/or release of nucleic acids or other biological or non-biological molecules (e.g., proteins, small compounds, etc.) as desired. For example, according to one exemplary embodiment, the gels described herein may provide capture of nucleic acids from a dilute solution and then subsequently release them into a smaller volume to create a more concentrated solution, which may be preferred in further applications.

Figure 4:
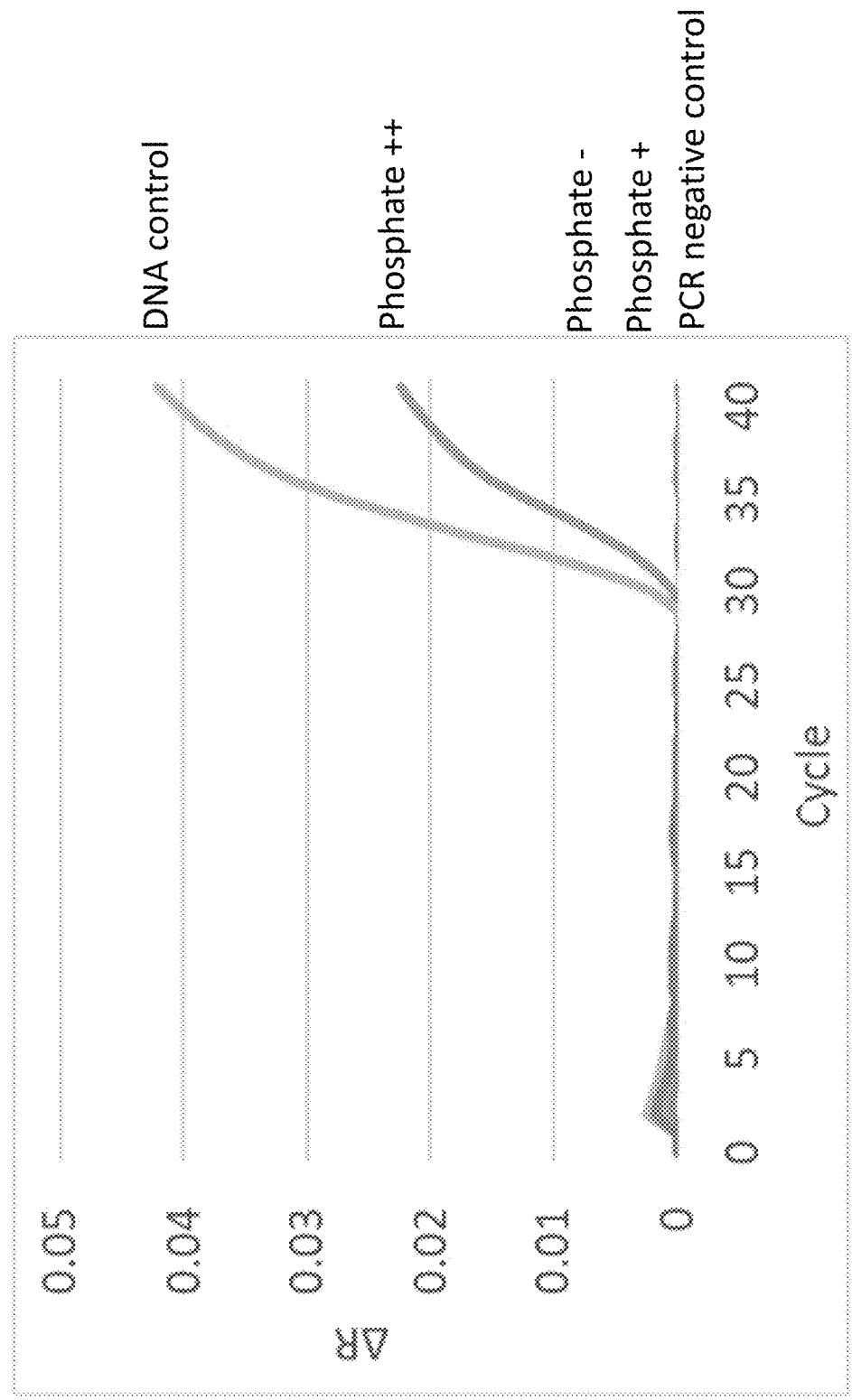
FIG. 4 is a plot illustrating elution of nucleic acid bound to a gel according to an exemplary embodiment.

For example, FIG. 4 shows an exemplary embodiment in which nucleic acid was adsorbed by a gel and selectively released in the presence of phosphate. Briefly, three replicates of a solution having equal amounts of humic acid and bacterial DNA was mixed with an aluminum hydroxide gel. The gel was collected and washed three times with water to remove any unadsorbed components. The washed gel was then resuspended in a solution containing no phosphate, a relatively low concentration of phosphate (50 mM), or a relatively high concentration of phosphate (500 mM). The gels were then pelleted by centrifugation and an aliquot of the supernatant was tested by qPCR. The results shown in FIG. 4 suggest that a significant amount of DNA was released from the gel in the presence of the high concentration of phosphate, while the humic acid remained substantially bound to the gel.

Example 5

Chelating agents are common components in biological buffers, such as lysis buffers. These chelating agents, such as ethylenediaminetetraacetic acid (EDTA), have been known to interfere with the ability of various metal-based substances to bind nucleic acid and/or contaminants. A similar procedure to those above was performed in the presence or absence of EDTA to investigate the effect this chelating agent may have on the adsorption abilities of the gel.

Figure 5:
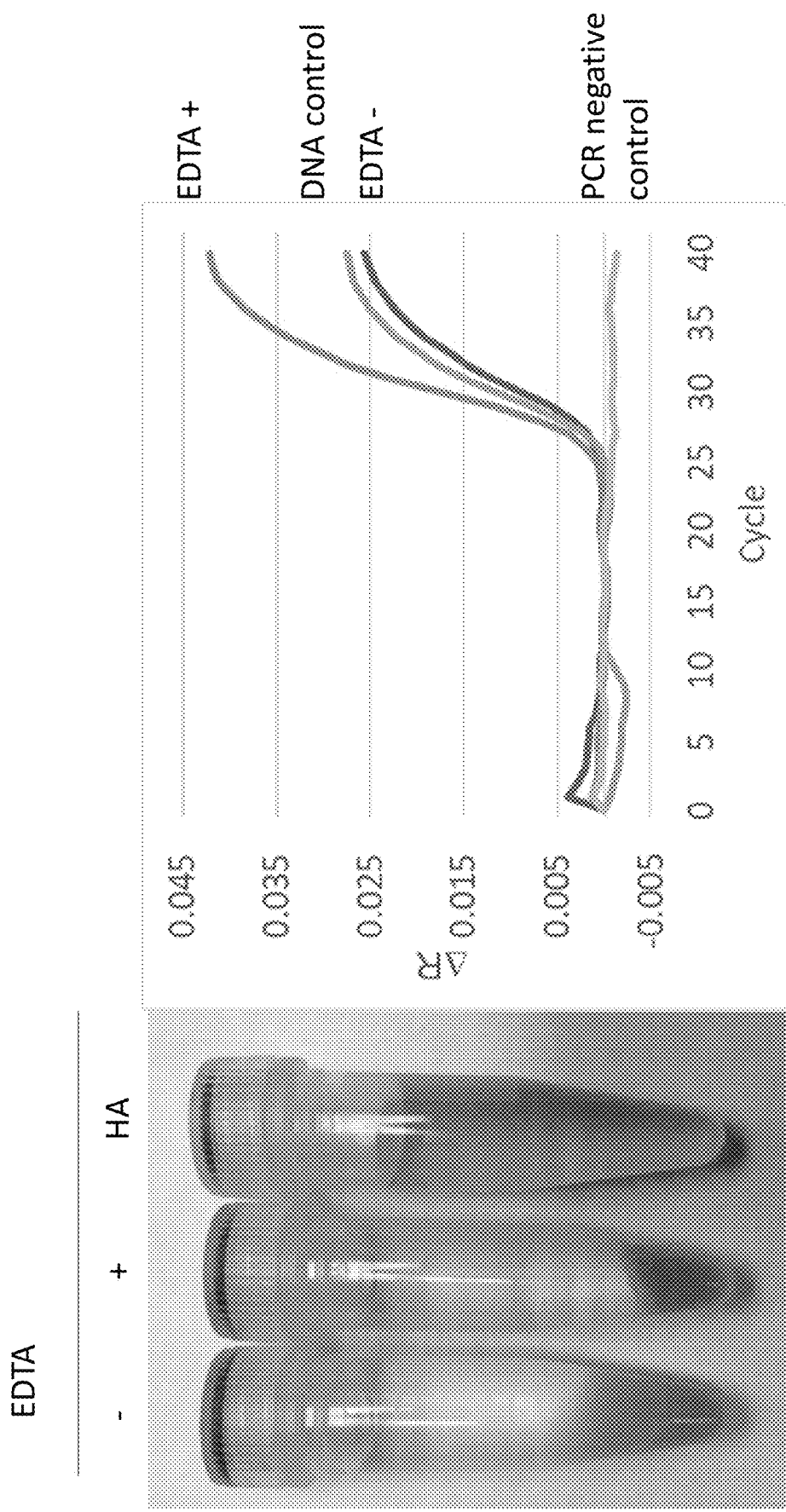
FIG. 5 is a photo and plot illustrating the result EDTA has on the binding specificity of a gel according to an exemplary embodiment.

Briefly, solutions containing identical amounts of humic acid and DNA were treated with an identical volume of aluminum hydroxide gel and a suitable amount of phosphate. The ratio of $PO_4^{3-}:La^{3+}$ in the solutions was about 4:1, with a pH of 7.5. Samples either received no EDTA or 100 mM EDTA. After mixing, the solutions were spun down, and an aliquot of the supernatant was subjected to qPCR As can be seen in FIG. 5, the presence of EDTA did not appear to affect the ability of the gel to bind humic acid.

Figure 6:
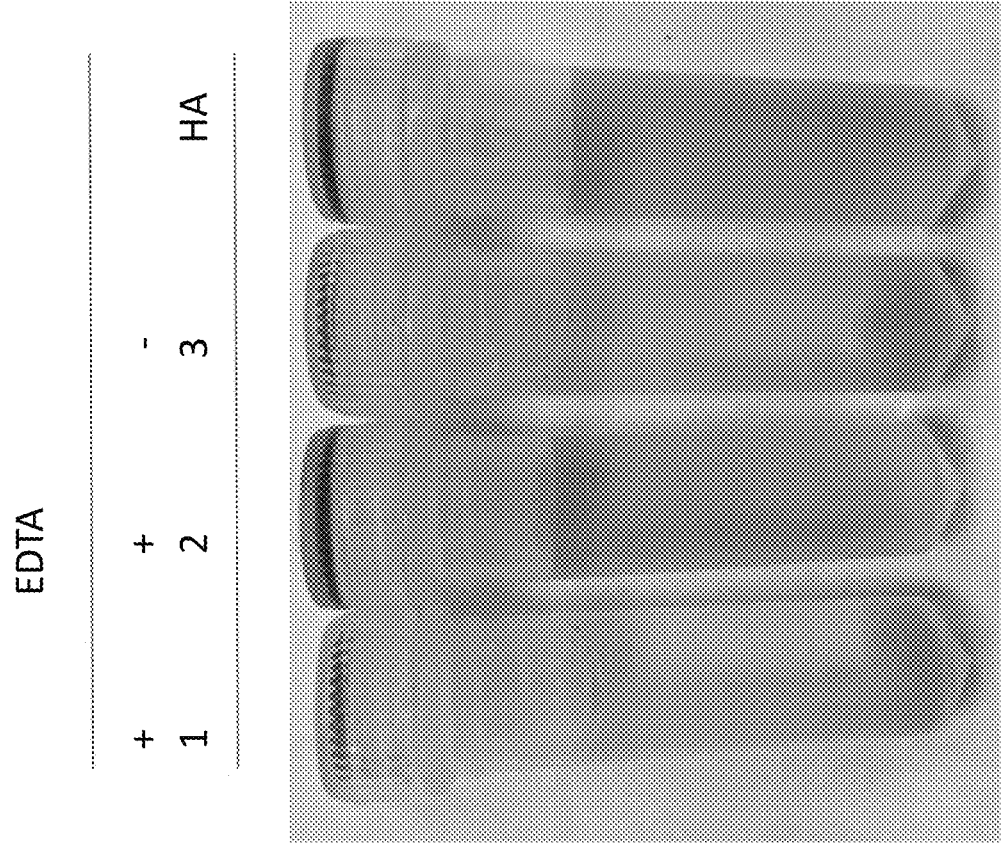
FIG. 6 is a photo illustrating the result EDTA has on the binding specificity of a gel according to an exemplary embodiment and to a commercially available metal-based DNA purification resin.

In a related experiment, the gel as described herein was compared to a commercially available DNA purification product that uses a metal salt for flocculation of contaminants. Briefly, equivalent solutions of humic acid were mixed with (1) an aluminum-based gel according to the exemplary embodiment along with 100 mM EDTA; or were treated with the commercially available metal salt-based DNA procedure with (2) or without (3) 100 mM EDTA. As can be seen in FIG. 6, the EDTA did not inhibit the gel according to an exemplary embodiment from binding the humic acid, as shown by the color change of the solution vs the control (HA). In contrast, the presence of EDTA negatively influenced the ability of the commercially available metal salt-based DNA purification procedure to flocculate the humic acid.

Example 6

Figure 7:
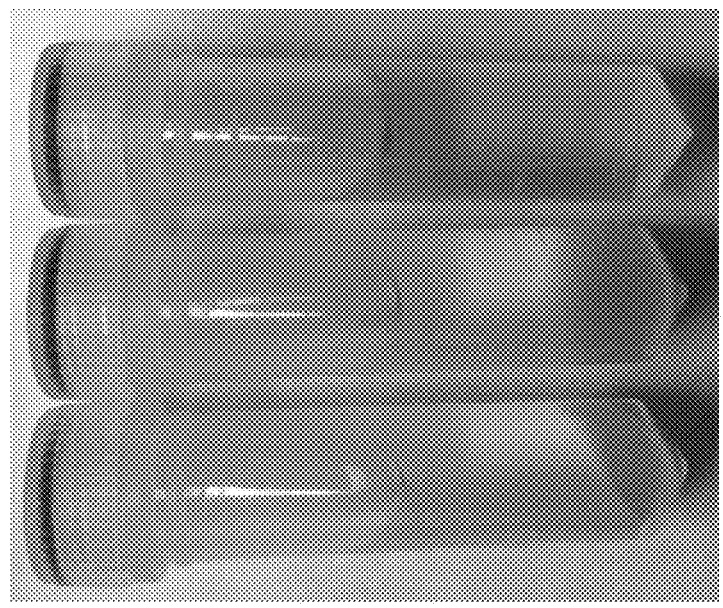
FIG. 7 is a photo illustrating the result freeze-drying the gel has on the binding specificity of a gel according to an exemplary embodiment.

The effect that freeze drying a gel might have on binding specificity was investigated. Briefly, ammonium aluminum sulfate $((NH_4)Al(SO_4)_2)$ was reacted with sodium hydroxide (NaOH) to form an aluminum hydroxysulfate gel, which was then collected by centrifugation and washed five times with water to remove unreacted components. After the final wash, the gel was resuspended in a solution containing a final concentration of 20% trehalose. This gel suspension was then aliquoted, snap frozen in liquid nitrogen, and then freeze-dried in a Labconco Triad freeze drying unit for approximately 48 hours. An equal amount of humic acid was mixed with no gel, a freshly prepared gel, or a freeze-dried gel rehydrated in water. As can be seen in FIG. 7, the freeze-dried gel, when rehydrated, provides similarly effective binding ability of humic acid when compared with freshly prepared gels.

Example 7

The effect of the molar ratio of phosphate to $Cs^{3+}$ in the gel during adsorption was investigated.

Briefly, cesium phosphate gel was made by mixing 50 µl of CsCl solution (1M) with 50 Id, 100 µl, 150 µl, or 200 µl of phosphate solution (M, pH 7.5) in individual tubes. The resulting ratios of $PO_4^{3-}:Cs^{3+}$ were 1:1, 2:1, 3:1, and 4:1, respectively. Each tube received 10 µl Control DNA solution, 8 µl Humic Acid solution (12 mg/mi), up to 1 ml water, and vortexed to mix. After 10 minutes of mixing at room temperature, the tubes were spun down, and 1 µl of the supernatant from each tube was subject to qPCR.

Figure 8:
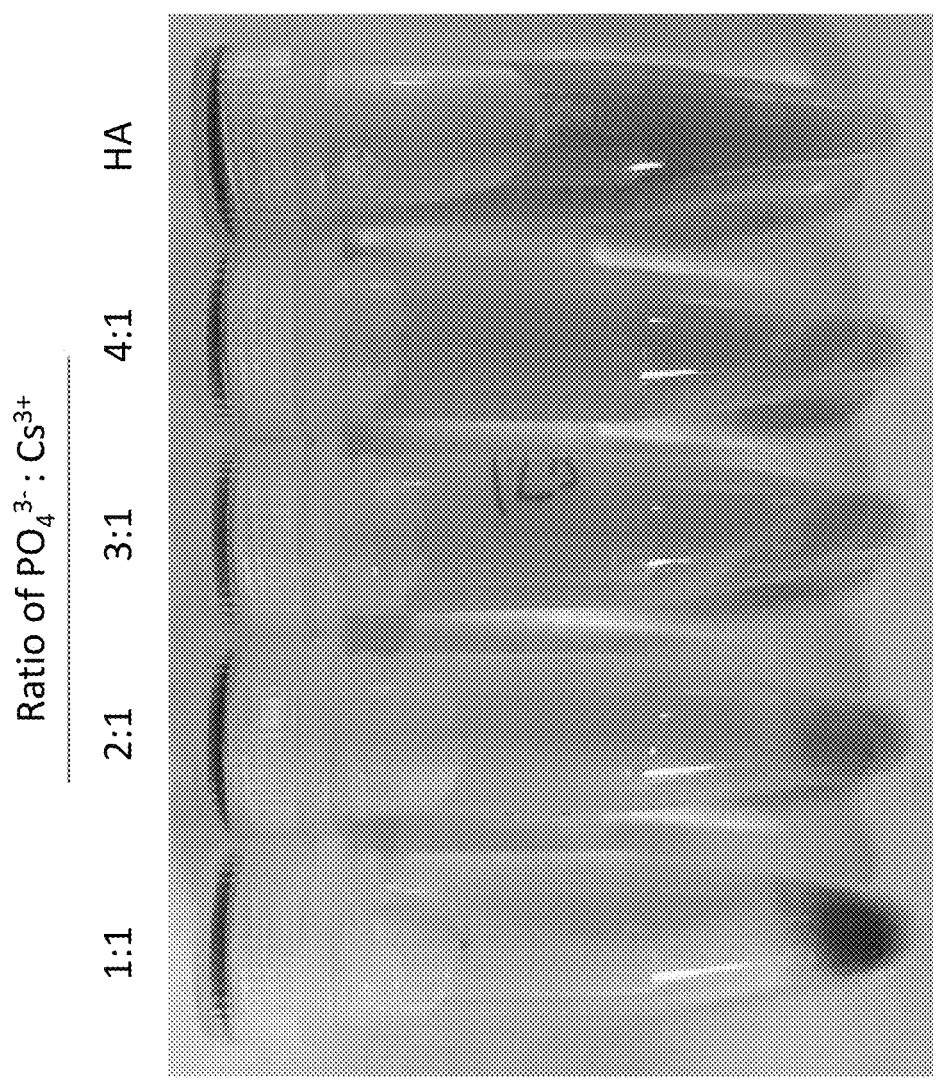
FIG. 8 is a photo illustrating the result various phosphate to metal ratios have on the binding specificity of a gel according to an embodiment.

As can be seen from FIG. 8, a lower ratio of $PO_4^{3-}:Cs^{3+}$ results ineffective removal of humic acid, but binds less at a higher ratio.

What is claimed is:

1. A method of removing contaminants from a nucleic acid containing sample, the method comprising the step of:
    obtaining a metal-based gel produced by reacting a 3+ metal salt with a base, phosphate, or a combination thereof;
    contacting the sample with the metal-based gel to bind the contaminants to the metal-based gel; and
    reducing adsorption of the nucleic acids to the metal-based gel by modulating the phosphate concentration, phosphate:metal ratio, and/or pH in the sample during the contacting.

2. The method according to claim 1, wherein the metal-based gel is an aluminum-based gel, a lanthanum-based gel, or a combination thereof.

3. The method according to claim 1, wherein the metal-based gel is an aluminum hydroxide gel, an aluminum phosphate gel, an aluminum hydroxyphosphate gel, a lanthanum hydroxide gel, a lanthanum phosphate gel, a lanthanum hydroxyphosphate gel, or any combination thereof.

4. The method according to claim 1, wherein the concentration of phosphate in the sample during the contacting is 2 mM to 200 mM.

5. The method according to claim 1, wherein the pH of the sample during the contacting is 2 to 11.

6. The method according to claim 1, wherein a molar ratio of phosphate to metal in the gel during the contacting is 10:1 to 1:100.

7. The method according to claim 1, further comprising the step of separating the nucleic acids from the metal-based gel containing the bound contaminants.

8. A method for binding contaminants from a nucleic acid containing sample, the method comprising the steps of:
    contacting a nucleic acid containing sample contaminated with contaminants with a 3+metal salt, a base, phosphate, or a combination thereof to form a metal-based gel;
    modulating the phosphate concentration, phosphate:metal ratio, and/or solution pH in the sample to bind the contaminants to the metal-based gel and reduce adsorption of the nucleic acids to the metal-based gel.

9. The method according to claim 8, wherein the metal-based gel is an aluminum-based gel, a lanthanum-based gel, or a combination thereof.

10. The method according to claim 8, wherein the metal-based gel is an aluminum hydroxide gel, an aluminum phosphate gel, an aluminum hydroxyphosphate gel, a lanthanum hydroxide gel, a lanthanum phosphate gel, a lanthanum hydroxyphosphate gel, or any combination thereof.

11. The method according to claim 8, wherein the concentration of phosphate in the sample during the contacting is 2 mM to 200 mM.

12. The method according to claim 8, wherein the pH of the sample during the contacting is 2 to 11.

13. The method according to claim 12 wherein the pH is 7.5 or greater than 7.5.

14. The method according to claim 8, wherein a molar ratio of phosphate to metal in the gel during the contacting is 1:100 to 10:1.

15. The method according to claim 14, wherein the molar ratio of phosphate to metal in the gel during the contacting is 1:100 to 4:1.

16. The method according to claim 8, further comprising the step of separating the nucleic acids from the metal-based gel containing the bound contaminants.

17. The method according to claim 1 wherein the metal-based gel is freeze-dried metal-based gel and rehydrating the freeze-dried metal-based gel before the contacting.

18. The method according to claim 5 wherein the pH is 7.5 or greater than 7.5.

19. The method according to claim 6, wherein the molar ratio of phosphate to metal in the gel during the contacting is 2:1, 3:1, or 4:1.

* * * * *